(12) United States Patent
Kuhn

(10) Patent No.: US 8,708,942 B2
(45) Date of Patent: Apr. 29, 2014

(54) CUSTOM ANKLE BRACE SYSTEM

(76) Inventor: Jeffrey Andrew Kuhn, Pittsburgh, PA (US)

( * ) Notice: Subject to any disclaimer, the term of this patent is extended or adjusted under 35 U.S.C. 154(b) by 328 days.

(21) Appl. No.: 12/703,549

(22) Filed: Feb. 10, 2010

(65) Prior Publication Data

US 2011/0196276 A1   Aug. 11, 2011

(51) Int. Cl.
*A61F 5/00* (2006.01)

(52) U.S. Cl.
USPC .............. 602/27; 602/6; 602/7; 602/23

(58) Field of Classification Search
USPC ............ 602/5–7, 23, 27, 60–62, 65; 128/882; 36/71, 89, 90, 93; 264/222, 223, 294, 264/248, 257, 258
See application file for complete search history.

(56) References Cited

U.S. PATENT DOCUMENTS

| | | |
|---|---|---|
| 3,906,943 A | 9/1975 | Arluck |
| 4,006,741 A | 2/1977 | Arluck |
| 4,060,075 A | 11/1977 | Blomer et al. |
| 4,136,686 A | 1/1979 | Arluck |
| 4,169,469 A | 10/1979 | Arluck |
| 6,025,414 A | 2/2000 | Rich |
| 6,093,161 A | 7/2000 | Vlaeyen et al. |
| 6,155,997 A * | 12/2000 | Castro ............... 602/27 |
| 6,726,645 B1 | 4/2004 | Davis |
| 6,793,640 B1 * | 9/2004 | Avon ................ 602/23 |
| 7,640,680 B1 * | 1/2010 | Castro ............... 36/140 |
| 2004/0034316 A1 | 2/2004 | Castro |
| 2006/0004313 A1 | 1/2006 | Heinz et al. |
| 2007/0004993 A1 | 1/2007 | Coppens et al. |
| 2007/0197948 A1 * | 8/2007 | Ingimundarson et al. ...... 602/27 |
| 2007/0203441 A1 | 8/2007 | Castro |
| 2008/0249446 A1 | 10/2008 | Baumgartner et al. |

* cited by examiner

*Primary Examiner* — Patricia Bianco
*Assistant Examiner* — Keri J Nelson
(74) *Attorney, Agent, or Firm* — Neal P Pierotti; Mentz, Lewis, Brodman, Must, O'Keefe

(57) ABSTRACT

A custom ankle brace system is disclosed which is constructed from a low temperature non-olefinic elastomeric blend material, and methods of fabricating and fitting the same. This material can be molded directly to a custom mold made from a casting of an affected body part. The final product will be an ankle brace that is able to be heated at low temperature (150° F.-200° F.) by use of an oven or equivalent, and custom molded directly on the patient. If necessary reheated, the ankle brace may be remolded to account for a change in the patient's anatomy or for an increase in comfort.

18 Claims, 11 Drawing Sheets

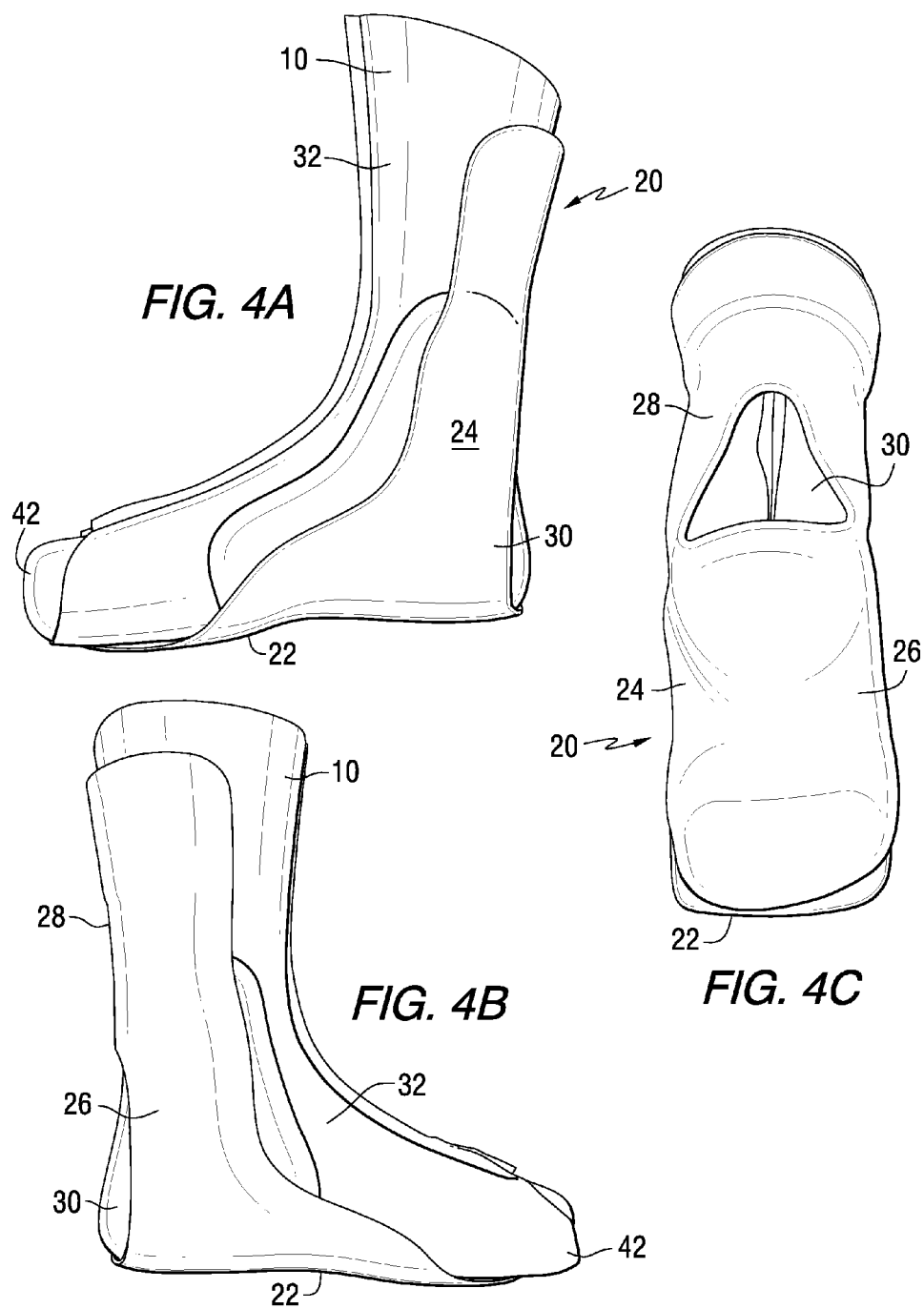

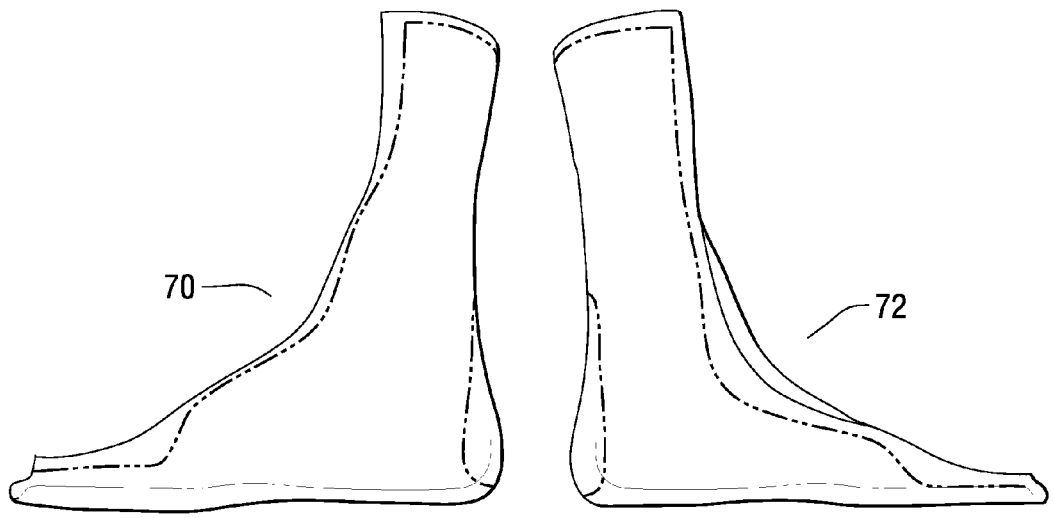
*FIG. 10A*  *FIG. 10B*
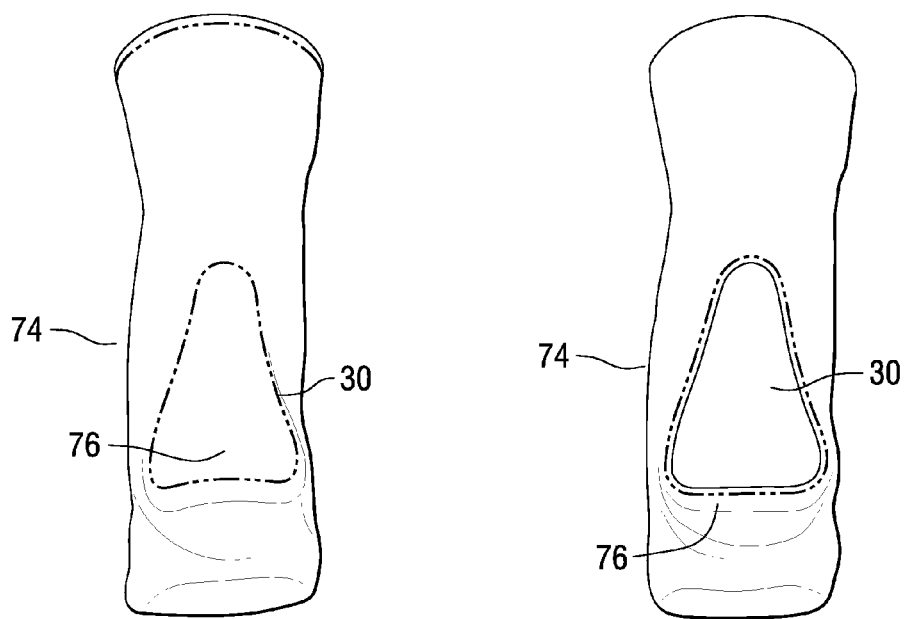
*FIG. 10C*  *FIG. 10D*

CUSTOM ANKLE BRACE SYSTEM

BACKGROUND OF THE INVENTION

1. Field of the Invention

The present invention relates generally to a custom ankle brace system and a method of fabricating the same.

2. Description of the Prior Art

Individuals with certain types of foot and/or ankle conditions often suffer from limited mobility and require the use of braces or other aids for walking. These conditions often require the immobilization of the foot and/or ankle or at least partial restriction of movement of the foot in the ankle or joint area. Immobilization is accomplished through the use of braces, orthotics or other devices.

Currently, orthotic devices for the foot and ankle are custom fabricated by applying and fitting the orthotic device to a duplicate model of the affected patient's limb. The degree to which a custom device fits the patient and is comfortable to wear depends on the experience and skill level of the professional taking a cast of the affected limb, the accuracy any measurements taken and the technician who must work from the information provided to fabricate the custom device. The various methods for constructing the duplicate model of the patient's affected limb sometimes results in be inaccurately sized and shaped casts. Inaccuracies are caused by variables in casting methods, such as applying the casting bandage too loose or too tight, imprecise measurements of the affected limb and the translation of information during mold production. These uncertainties can result in a final product that is not intimate in fit and lacks comfort, stability and utility.

A second issue affecting the quality of a custom molded ankle brace is the type of materials utilized in the manufacture of the orthotic device. The materials currently used for production tend to be thick and bulky. For instance, many of the current lace or gauntlet devices use cowhide leather inner liners and/or outer layers. Authentic leather is not uniform in thickness and will therefore result in a product with inconsistent size and shape. Many of these devices are also manufactured using solvent based adhesives, such as master's cement or an equivalent.

Typically, a series of presized blank brace support units are constructed, which are intended for further customization based upon the particular patient's needs. The thermoplastics used for manufacturing the support portions of the brace are difficult to remold or reshape during this customization. The most commonly used thermoplastics in the orthotic industry require high temperatures to shape and mold. These plastics are difficult to adjust after the initial molding and cumbersome to handle due to the high temperatures required to re-soften the material so that it becomes malleable. Alternatively, low-temperature thermoplastics in use tend to become flaccid and lose their pre-molded shape when reheated. In addition, these low temperature plastics tend to become gummy and self-sticking. Thus, reworking the material to conform to a particular patient often results in a loss of rigidity and a decrease in support. Because the current plastics are not amenable to adjustment, it is also difficult to grossly adjust the device in response to a change in the patients' anatomy due to growth or swelling of the limb. Instead, only spot heating and adjustment is possible. Many patients, such as children, are forced to purchase orthotic devices frequently due to the changing size of their limbs as they age. Lastly, many prior art devices, as a result of the non-uniform materials and the strength characteristics of the thermoplastics used in production, must be constructed at a greater thickness to provide the degree of rigidity and support needed.

The device in Castro, U.S. Patent Application Publication No. 2004/0034316 and U.S. Patent Application Publication No. 2007/0203441, comprises a unitary, heat-moldable ankle and arch support system encased in leather. The device is manufactured from a flat sheet of plastic material which is molded into pre-shaped and pre-sized ankle braces. The plastic material is folded along the bottom of the foot, excluding the heel, and then upward along the ankle and leg. The back of the leg is left uncovered by the plastic so that the orthotic may be properly molded, thus decreasing the rigidity of the orthotic. In addition, the patient's heel is left unsupported by the plastic material because the bottom portion of the plastic support does not extend to entire length of the sole of the foot. The brace is covered with a material such as leather and then heated in boiling fluids before fitting over the foot of an individual. The thermoplastic material described comprises an olefinic polymer. Olefin, also known as polypropylene or polyethylene is a long-chain polymer synthetic fiber. It is produced by the polymerization of ethylene and/or propylene gases under very specific conditions. Olefinic polymers loose their rigidity and strength at the temperatures required for remolding. The olefinic material must therefore be used at a greater thickness in order to provide adequate support. Finally, the procedure of heating the orthotic in boiling water or liquid will affect any cover materials, for instance leather coverings, which in turn interfere with the fitting process.

Thus, a need exists for a custom made orthotic device that is fabricated out of thinner material without a loss in strength. Such a device would be capable of becoming malleable at a temperature low enough so the material may be custom molded on the affected limb without harming the patient. The device would keep its general shape and integrity when reheated but remain pliable enough to mold onto an affected body part. The device would insure an intimate fit, achieve a true duplication of the patient's anatomy, and provide low profile support.

SUMMARY OF THE INVENTION

An orthotic device is provided that, once fabricated can be heated at a low temperature, for instance 150-200 degrees Fahrenheit, and readjusted for the proper fit and comfort of a patient. The device becomes soft and moldable so that it may be molded directly on the patient. This results in a realistic duplication of the anatomy for which the device is intended. Once cooled, the material returns to the rigidity needed for appropriate support while retaining its new molded shape. The device utilizes relatively thin materials possessing better strength to thickness characteristics than thicker, low temperature thermoplastics. The ankle brace may be reheated to allow for adjustment for growth or swelling of the limb or to provide added comfort The present device utilizes a non-olefinic elastomeric blend thermoplastic polymer support for the construction of a custom ankle brace. The thermoplastic support comprises a back portion and sole portion adjacent to and formed integrally with the back portion. The sole portion of the thermoplastic support provides support to substantially all of the sole and heel of a user's foot. The ankle brace may be adjusted to treat different clinical conditions. For example, the thermoplastic support may extend to varying degrees around the front of the leg and ankle and to varying degrees up the calf. The thermoplastic support may contain ankle hinges to aid in the bending of the ankle. The thermoplastic support may also have cut-outs for the toe and heel portions of the foot. The ankle brace utilizes an inner liner, foam pads and a flexible outer layer for additional comfort and support. The ankle brace may be tightened around the foot and ankle through the use of, for example, eyelets and laces.

The present invention also encompasses methods for making the custom ankle brace. The methods include the steps of covering a replica mold of a foot and ankle with an inner lining and foam pads to add comfort and support. Next, a non-olefinic elastomeric blend polymer material is heated so that the material becomes soft and flexible. The non-olefinic material is then shaped around and secured to the inner lining and foam pads to form into a thermoplastic support, comprising a back portion and sole portion adjacent to the back portion. The sole portion of the thermoplastic support provides support to substantially all of the sole and heel of a user's foot. The sole portion is adjacent to and formed integrally with the back portion. A flexible outer layer is then secured to the thermoplastic support to provide protection and support to the custom ankle brace. Ankle hinges may be added to the thermoplastic support to aid in the flexing of the ankle. Cut-outs for the toe and posterior heel portions of the foot may also be added to the thermoplastic support. In addition, a lacing or other type of securing system may be added to the ankle brace to allow for tightening around the foot and ankle.

The invention further contemplates a method of fitting and/or using a custom ankle brace system, the first step comprising obtaining a replica of the foot and ankle for which the brace is to be prepared. Next, a custom ankle brace is prepared utilizing the method of the present invention. The ankle brace comprises a thermoplastic support with a back portion and sole portion adjacent to the back portion. The sole portion of the thermoplastic support provides support to substantially all of the sole and heel of a user's foot. In the next step, the ankle brace is heated to a temperature from about 150° F. to 200° F. The patient's foot is then placed in a clinically desirable position and the heated ankle brace is placed on the foot and ankle. The ankle brace is the compressed and fitted on the foot and ankle of the patient. The ankle brace may be refitted and adjusted by repeating the heating and compressing/fitting steps as described above.

DESCRIPTION OF THE DRAWINGS

FIG. 4A shows a medial view of the thermoplastic support of the present invention.

FIG. 4B shows a lateral view of the thermoplastic support of the present invention.

FIG. 4C shows a posterior view of the thermoplastic support of the present invention.

FIG. 10A shows the medial malleolus trace lines on the thermoplastic support of the present invention.

FIG. 10B shows the lateral malleolus trace lines on the thermoplastic support of the present invention.

FIG. 10C shows the navicular trace lines on the thermoplastic support of the present invention.

FIG. 10D shows the heel-cut out portion of the thermoplastic support of the present invention.

DESCRIPTION OF THE PREFERRED EMBODIMENTS

The primary feature of the present invention is an orthotic device that once fabricated can be heated at a low temperature (150-200 degrees Fahrenheit) in dry heat, for instance in an oven or equivalent. The device will soften and become pliable and moldable so that it may be molded directly on the patient by use of the lacing/strapping system or by binding with an elastic bandage or equivalent. This results in a molded, realistic duplication of the anatomy for which the device is intended. Once cooled, the material returns to the rigidity required to provide appropriate support while holding its new molded shape. Another advantage of the present device is the ability to utilize thinner materials possessing similar strength characteristics as the thicker versions of thermoplastics used in the prior art.

Figure 1:
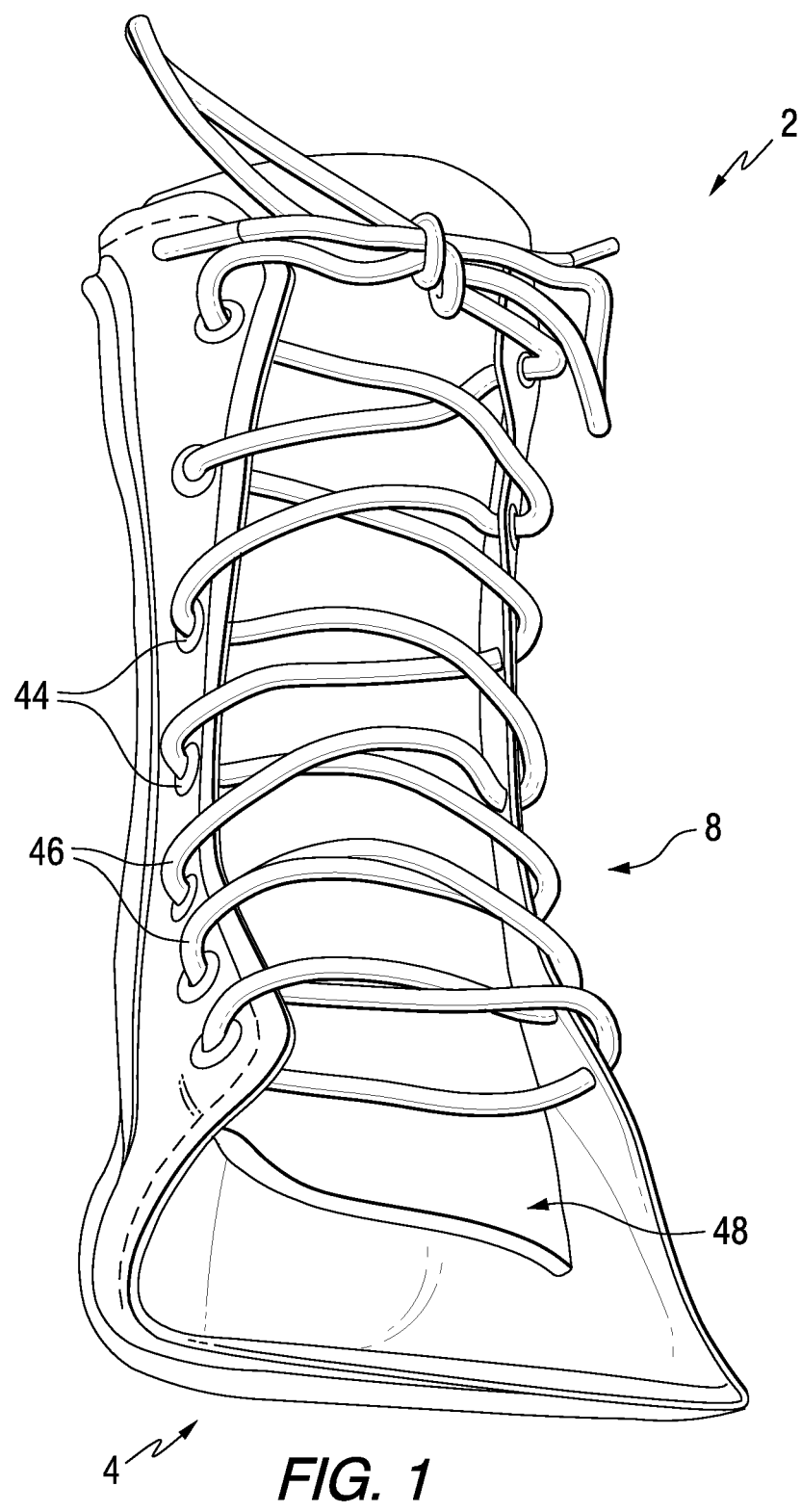
FIG. 1 shows a front perspective view of the custom ankle brace of the present invention.

FIG. 1 illustrates the custom ankle brace 2 of the invention. Ankle brace 2 is constructed of materials with less bulk than those of the prior art so that ankle brace 2 can comfortably fit into the patient's current shoe. The high temperature thermoplastics used in the orthotic industry require high temperatures to shape and mold. Alternatively, low-temperature thermoplastics in use tend to become flaccid and lose their premolded shape when reheated. In addition, these low temperature plastics tend to become gummy and self-sticking. Olefinic thermoplastics, commonly used in orthotic devices, must be heated at temperatures over 210° F. in order for them to become soft enough to mold. However, many olefinic thermoplastics can not be heated on multiple occasions without breaking down their components. To solve this problem, thermoplastic support 20 of the present invention is comprised of a non-olefinic elastomeric blend polymer material, as described below in reference to FIGS. 4A, 4B and 4C. Thermoplastic support 20 becomes soft and pliable when heated at a range of between about 150-200° F., i.e., below the boiling point of a liquid. The non-olefinic polymer retains its structural integrity at these temperatures. Unlike the orthotic thermoplastics of the prior art, the present thermoplastic won't become gummy or self sticking, but will retain its structural integrity. The non-olefinic elastomeric blend cools quickly and then retains its shape. This substance may be heated and cooled multiple times without compromising the integrity of the material or breaking down the components of the polymer blend. This results in a fully adjustable ankle brace system 2 which can be repeatedly heated and adjusted to account for growth of the patient or swelling of the limb or to provide greater comfort.

In addition, many prior art orthotic devices utilize cowhide leather inner liners and/or outer layers. Authentic leather is not uniform in thickness and will therefore result in a product with inconsistent size and shape. The present invention uses a soft and flexible synthetic suede fabric for the inner liner. These material have a consistent thickness and will therefore not add additional bulk to the orthotic. Ankle brace 2 also utilizes foam pads 12 to protect protruding portions of the ankle and foot, as described in more detail in reference to FIGS. 3A, 3B and 3C. Foam pads 12 make the use of a complete or continuous inner liner unnecessary, thus decreasing the bulk of ankle brace 2.

In one embodiment, ankle brace 2 generally consists of a toeless portion 4. Preferably, custom ankle brace 2 of the invention consists of four layers: an inner liner, a foam liner, a thermoplastic support, and outer layer. Ankle brace 2 also comprises a closure apparatus 8 for securing ankle brace 2 to the foot and ankle of the patient. In one embodiment as illustrated in FIG. 1, closure apparatus 8 comprises eyelets 44 and laces 46. Ankle brace 2, as embodied in FIG. 1, covers the foot, ankle, lower calf, upper foot and mid foot, with an opening 4 for the toes. One of ordinary skill in the art will understand that alternative configurations of ankle brace 2 are contemplated, for instance a brace that does not cover the entire upper foot, or calf area, or a device that completely or partially covers the toe area.

Figure 2:
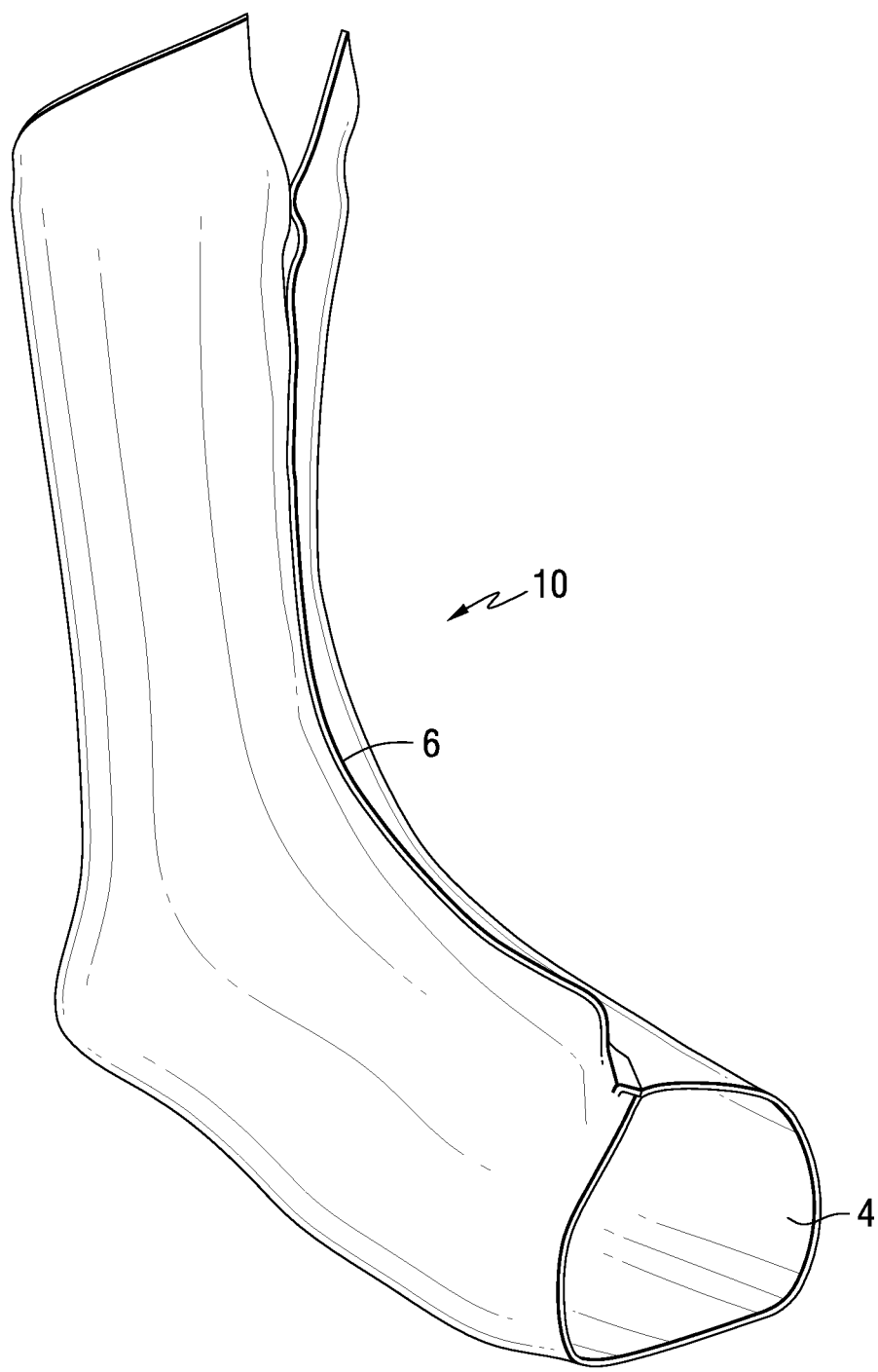
FIG. 2 shows a perspective view of the inner liner of the present invention.

FIG. 2 illustrates inner liner 10. Here, inner liner 10 is arranged to cover the foot, ankle, lower calf, upper foot and mid foot, with an opening 4 for the toes. One of ordinary skill in the art will understand that alternative configurations of inner liner 10 are contemplated, for instance an inner liner that does not cover the entire upper foot, or calf area. Seam 6 as illustrated in FIG. 2 will be opened down the entire front or anterior of ankle brace 2. Although FIG. 2 illustrates a single vertical seam 6, multiple seams 6 may be utilized, for instance in the case of a larger foot. This will allow for placement and attachment of ankle brace 2 to the foot and ankle, through the use of closure apparatus 8. In a preferred embodiment, inner liner 10 will lie between the patient's foot/ankle and the thermoplastic support. Inner liner 10 may be constructed from a variety of materials, with the understanding that material is strong, but thin and comfortable. Such materials may comprise, for example, cotton, polyester, leather and the like. In one embodiment, inner liner 10 is constructed from a soft and flexible synthetic suede fabric that will add minimal bulk to ankle brace 2. Inner liner is generally of a thickness of between 1.0 and 1.6 mil. Inner liner 10 may also contain closure apparatus 8, as discussed in more detail in reference to FIGS. 6A, 6B and 6C.

Figures 3A, 3B, 3C:
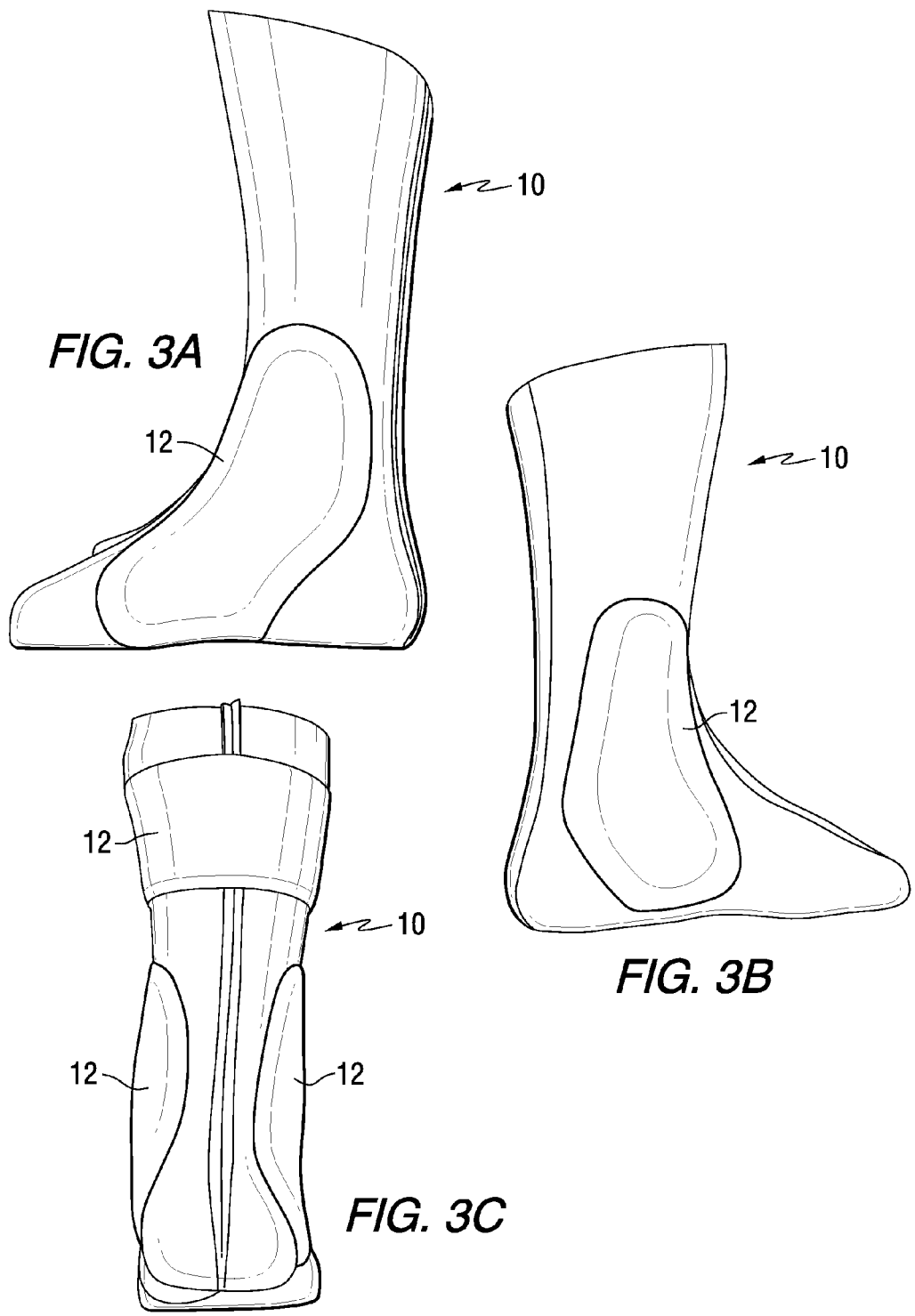
FIG. 3A shows a perspective view of the medial foam pads of the present invention.
FIG. 3B shows a perspective view of the lateral foam pads of the present invention.
FIG. 3C shows a perspective view of the posterior foam pads of the present invention.

Continuous use of orthotic devices can cause blisters and sores because of rubbing or chafing of the device against the boney portions of the affected limb. The present invention therefore utilizes a foam liner, or padding, to prevent these types of injuries. FIGS. 3A, 3B and 3C illustrate foam liner of the ankle brace 2. Foam liner comprises foam pads 12 placed on those portions of the ankle or foot that will rub or chafe against the ankle brace. Foam pads 12 are constructed of a soft material that will prevent this rubbing or chafing, such as Microcel Puff®, P-Cell™, Poron®, PPT and Aliplast™. In one embodiment, Foam pads 12 are constructed from Plastizote®, a closed cell cross-linked polyethylene foam, or equivalent. Foam pads 12 are shaped and placed over the medial malleolus (FIG. 3A), lateral malleolus (FIG. 3B) and navicular portions (FIG. 3C) of the foot and ankle. Foam pads 12 cover the protruding portions of the ankle and foot and thus provide comfort and protection from any rubbing or chafing of the ankle and foot. One of skill in the art will understand that additional pads may be placed on other portions of the ankle, foot or calf as needed to prevent rubbing or chafing. For instance, a foam pad 12 may be placed over the open portion of the heel region. Foam pads 12 make the use of a complete or continuous foam liner unnecessary, thus further reducing the bulk of the ankle brace. Foam pads 12 are secured to inner liner 2 with an adhesive, as illustrated in FIGS. 3A, 3B and 3C. The adhesive may comprise a variety of materials known to one of skill in the art that will allow pads 12 to bond with inner liner 2. The adhesive must become flexible when heated and then become rigid when cooled to insure proper bonding of all ankle brace 2 components. In a preferred embodiment, the invention utilizes a urethane adhesive which provides strength and water resistance without adding bulk. In addition, the urethane adhesive will bond to the non-olefinic thermoplastic support.

Figures 5A, 5B, 5C:
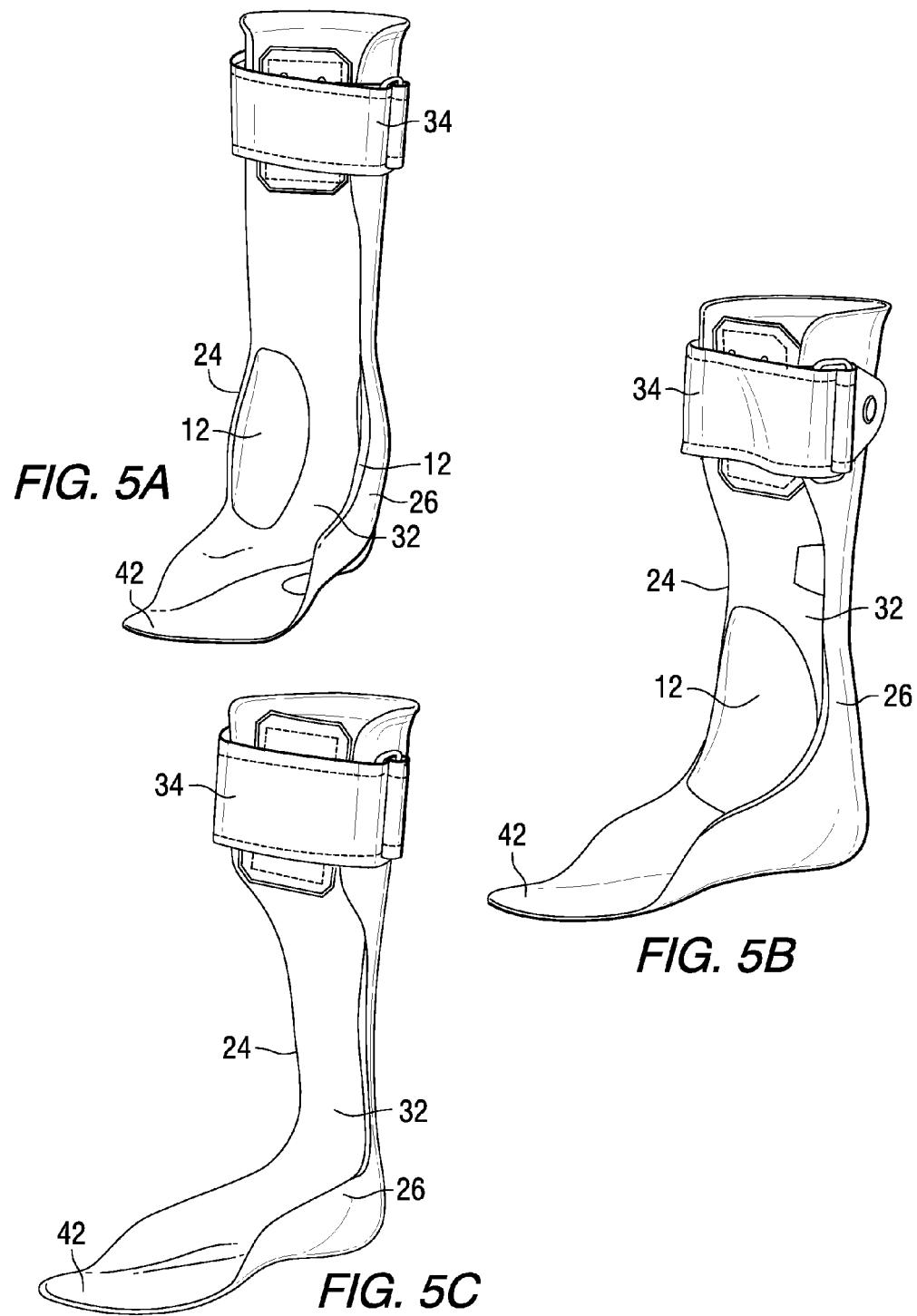
FIGS. 5A, 5B and 5C show the medial and lateral portions of thermoplastic extending around the calf to varying distances.

Referring now to FIGS. 4A, 4B and 4C, thermoplastic support 20 provides substantially rigid support for the foot, heel and ankle and the maintenance of the positioning of these structures. Thermoplastic support 20 consists of a sole portion 22 which is adjacent to the sole of the foot, a medial (inside) portion 24 that is adjacent to the medial portion of the lower calf, and a lateral (outside) portion 26 which is adjacent to the lateral portion of the lower calf. Sole portion 22 extends essentially along the entire sole of the foot, thus providing support to the entire sole and heel. Thermoplastic support 20 is structured to extend around the posterior portion of the calf, forming a continuous back portion 28 which provides support to the back part of the heel and the calf. Sole portion 22 extends outward from and is integrally formed with continuous back portion 28, thus providing increased support for ankle brace 2. In one embodiment, as illustrated in FIGS. 4A and 4B, the medial portion 24 and lateral portion 26 of thermoplastic support 20 extend around the posterior portion of the calf to approximately mid calf. One of skill in the art will recognize that the medial portion 24 and lateral portion 26 of thermoplastic support 20 can extend around the calf to varying distances as illustrated in FIGS. 5A, 5B and 5C. However, the medial portion 24 and lateral portion 26 do not extend completely around from the posterior portion of the calf, thus providing an uncovered portion 32 on the top of the foot and anterior portion of the calf. Uncovered portion 32 allows for the placement of closure apparatus 8. Medial portion 24 may be secured to lateral portion 26 by a securing mechanism 34 to insure a firm fit around the calf or ankle, as shown in FIGS. 5A, 5B and 5C. Securing mechanism 34 is configured to adjustably tighten the thermoplastic support 20 around the ankle and/or calf. Securing mechanism 34 may comprise, by way of example, straps, snaps, ties, or Velcro.

One of ordinary skill in the art will understand that alternative configurations of medial portion 24 and lateral portion 26 of thermoplastic support 20 are contemplated. For instance, the medial portion 24 and lateral portion 26 may not cover the entire upper foot or calf area.

FIG. 4C illustrates that continuous back portion 28 contains a heel cut-out portion 30. As a result, the plantar portion of the calcaneus is encompassed by the thermoplastic support while the posterior end is open. Heel cut-out portion 30 prevents rubbing and chaffing and allows for an easier fit due to decreased bulk. The heel of the patient still receives medial and lateral support because of the integration of continuous back portion 28 and sole portion 22 of thermoplastic support 20. In combination, these portions provide support to the medial and lateral parts of the ankle, as well as the heel of the foot. Heel cut out portion 30 may be covered by a foam pad 12 to prevent rubbing or chafing.

Thermoplastic support 20 is secured to inner liner 2 and foam liner 12 with the adhesive as described above. The adhesive may comprise a variety of materials known to one of skill in but must allow thermoplastic support 20 to bond to inner liner 2 and pads 12.

Figure 6A:
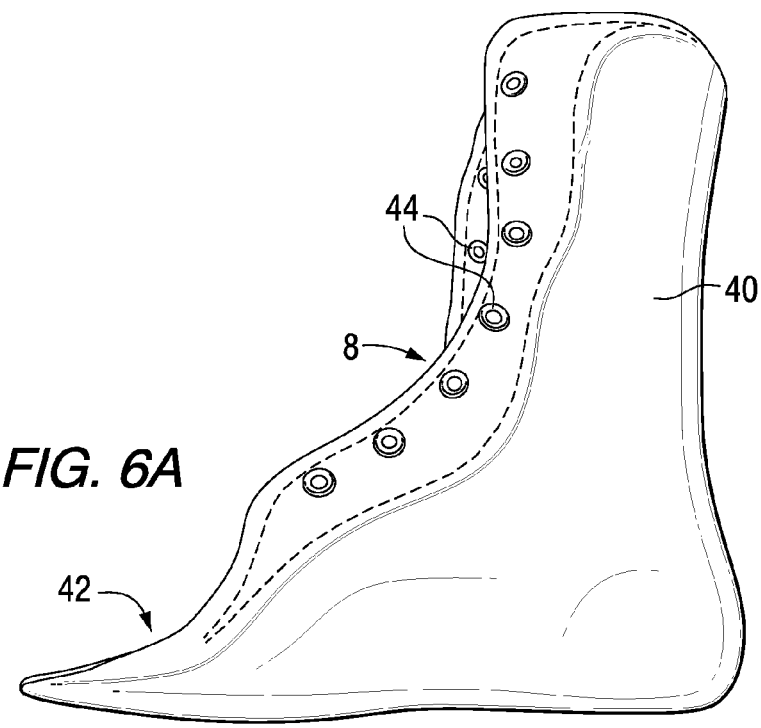
FIG. 6A shows a medial view of the custom ankle brace of the present invention.
Figure 6B:
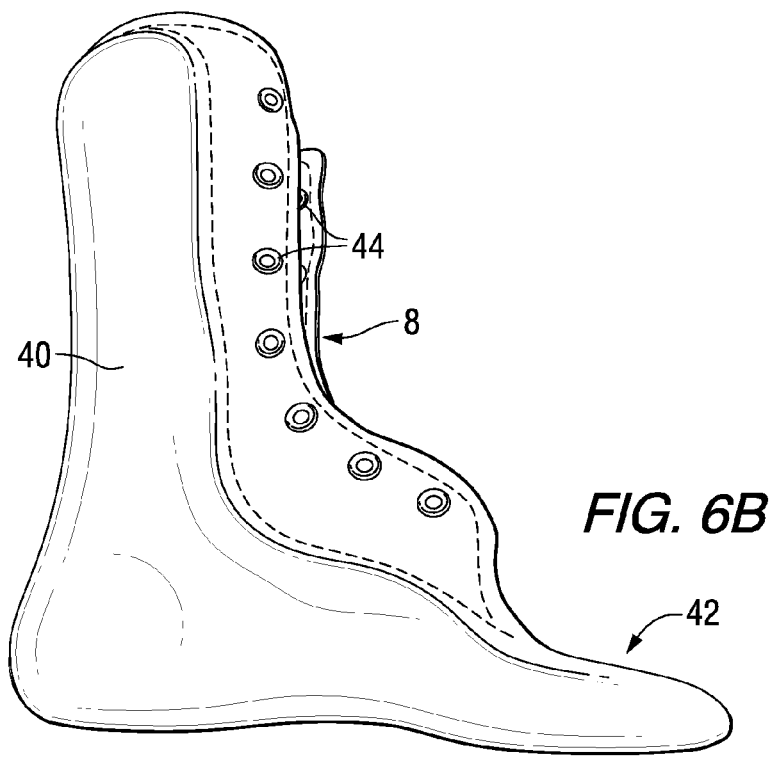
FIG. 6B shows a lateral view of the custom ankle brace of the present invention.

Shown in FIGS. 6A and 6B is the flexible outer layer 40. Outer layer 40 may be constructed from a variety of materials, with the understanding that material is strong but thin and comfortable. Such material may comprise, for example, cotton, polyester, leather, etc. Preferably, outer layer 40 is comprised from a flexible microfiber synthetic high abrasion resistant fabric, such as synthetic leather and suede made from nylon fiber and polyurethane. The use of these materials allows for the construction of an outer layer 40 which is resistant to environmental damages and which supplies an appropriate level of support to the leg of the patient. Outer layer 40 is of a thickness that will not add excess bulk to ankle brace 2, for instance from about 0.5 to 1.5 mm. It is preferable that outer layer 40 is positioned outside of and covers essentially all of thermoplastic support 20. One of ordinary skill in the art will understand that alternative configurations of ankle brace 2 are contemplated, for instance an outer layer that does not cover the entire upper foot, or calf area, or that completely or partially covers the toe area.

In one embodiment, outer layer 40 contains a toeless portion 42 which allows for easy fit into the patient's shoe or other footwear. Outer layer 40 also contains closure apparatus 8, as illustrated in FIG. 1. By way of example as illustrated in FIGS. 1, 6A and 6B, closure apparatus 8 comprises eyelets 44 which may be used to tighten and fasten ankle brace 2 around the foot and ankle, for instance through the use of laces 46. Other fastening devices are also contemplated, for example straps, snaps or Velcro. Closure apparatus 8 is configured to adjustably tighten ankle brace 2 around the ankle and calf. Outer layer 40 is secured to thermoplastic support 20 with the adhesive as described above. The adhesive may comprise a variety of materials known to one of skill in the art but must allow outer layer 40 to bond to thermoplastic support 20.

In one embodiment as illustrated in FIG. 1, outer layer 40 may further comprise a tongue 48 to enclose uncovered portion 32. Tongue 48 may be constructed of a variety of materials know in the art, such materials being soft but strong and flexible. In one embodiment, tongue 48 comprises headliner foam and a flexible microfiber synthetic high abrasion resistance fabric, such as synthetic leather.

One of skill in the art will understand that additional securing mechanisms 34 may be positioned to attach various parts of ankle brace 2 to each other. For instance, securing mechanisms may join inner liner 10 to flexible outer layer 40, closure apparatus 6 to flexible outer layer 40 or tongue 48 to flexible outer layer 40.

Figure 7:
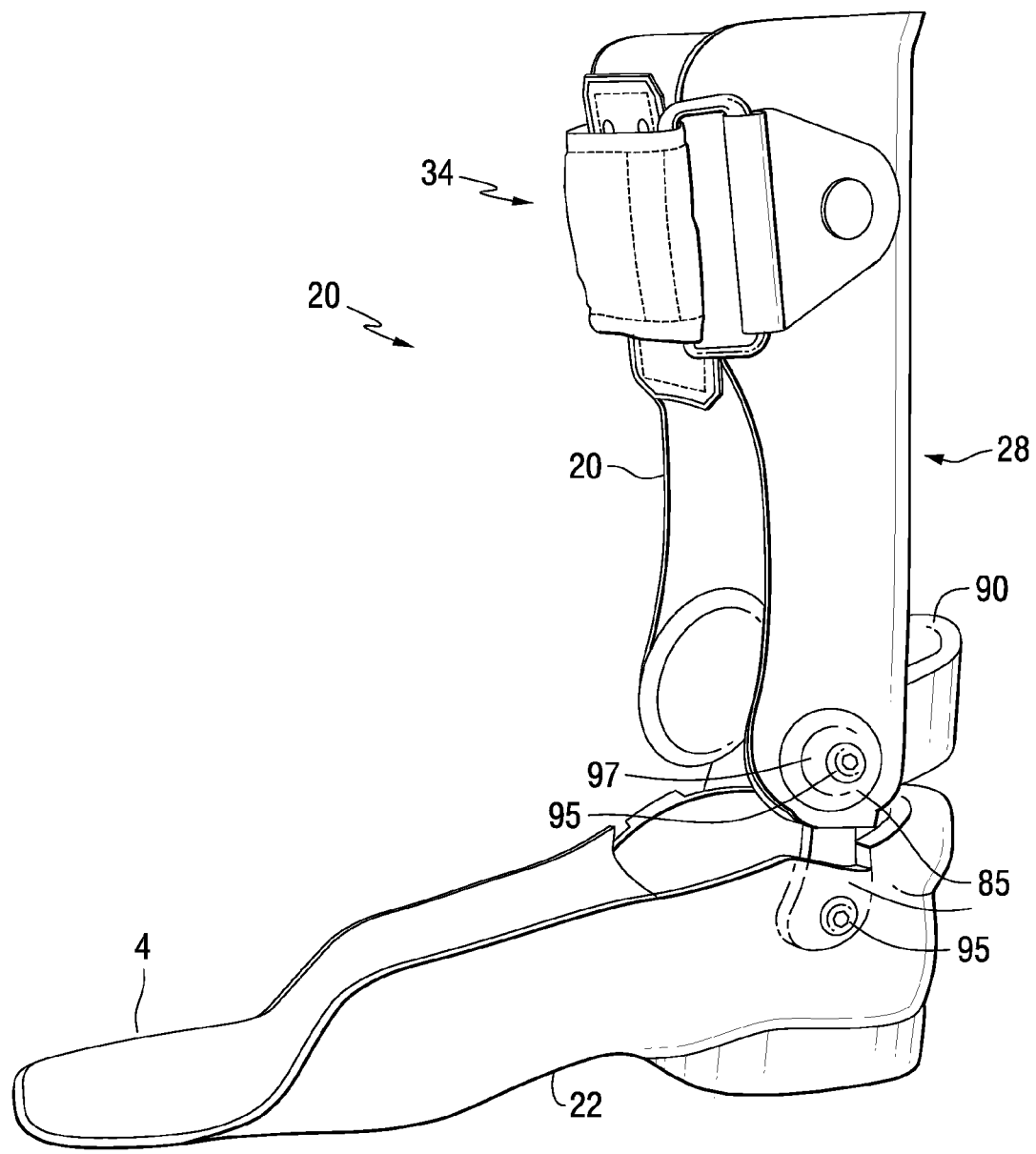
FIG. 7 shows a custom ankle brace of the present invention including an ankle hinge.

In an additional embodiment, ankle brace 2 may include one or more hinged ankle joints to assist with flexing of the ankle. As illustrated in FIG. 7, the thermoplastic support 20 of ankle brace 2 includes one or more hinges 85 that allow the ankle to flex. Hinge 85 comprises a urethane joint 97 attached by a metal screw 95. The urethane keeps its integrity at the temperatures used to produce, mold and adjust thermoplastic support 20 so that metal screw 95 is not displaced. The use of one or more hinges 85 allows for dorsiflexion, the movement in the ankle where the dorsal part (top) of the foot is moved in a manner towards the tibia. Hinges 85 also allow for plantarflexion, the movement which increases the approximate 90 degree angle between the front part of the foot and the shin. Medial and lateral movement of the foot and ankle are limited in this embodiment of the invention. In an additional embodiment, the hinged ankle joint illustrated in FIG. 7 may also include a posterior stop 90, which will limit plantarflexion. One of skill in the art will recognize that additional hinges 85 and posterior stops 90 may be used in a number of configurations so as to provide support as clinically necessary for the foot and ankle.

Figure 8:
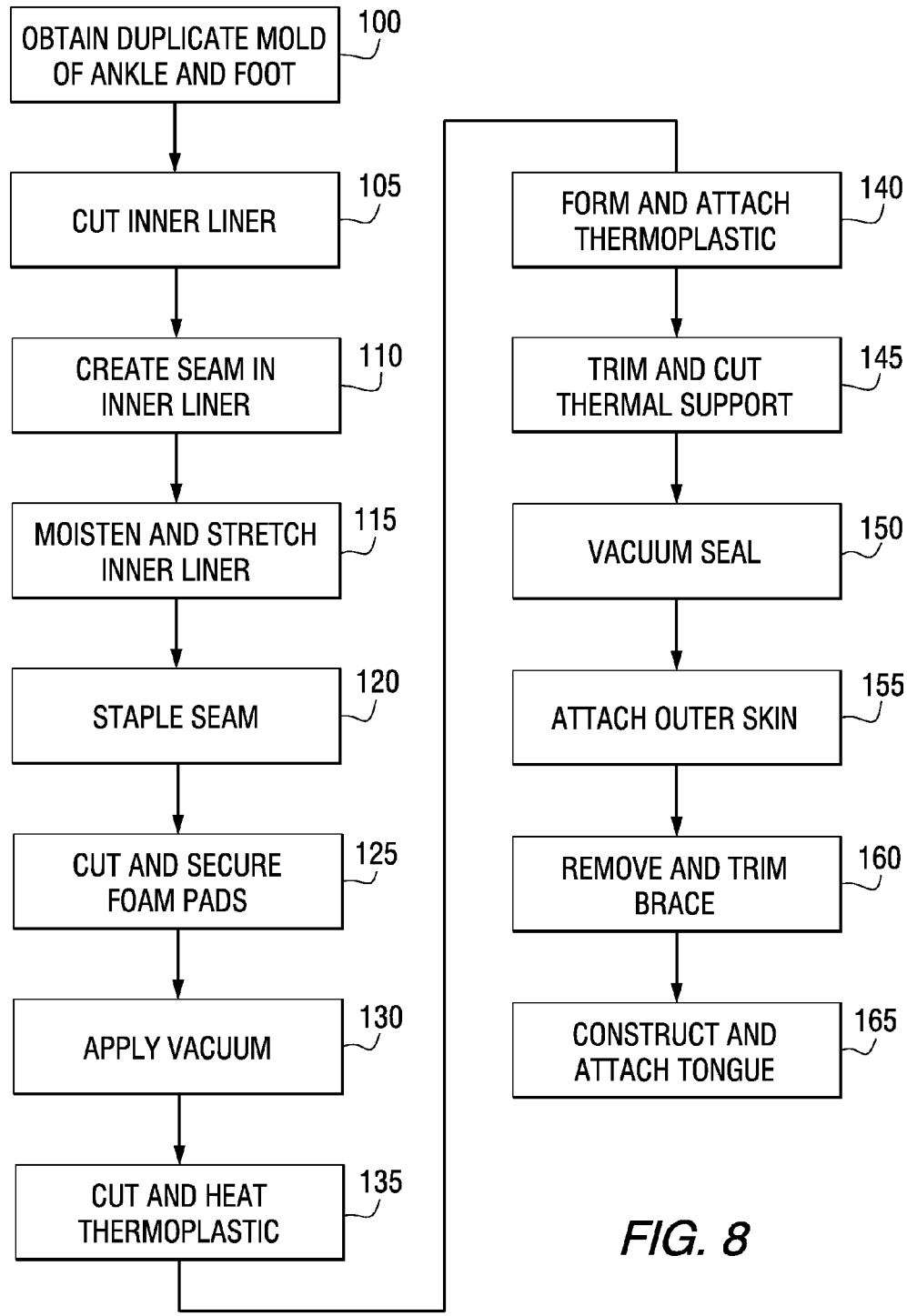
FIG. 8 shows an illustration of a diagram of an example of the steps in the preferred method.
Figure 9:
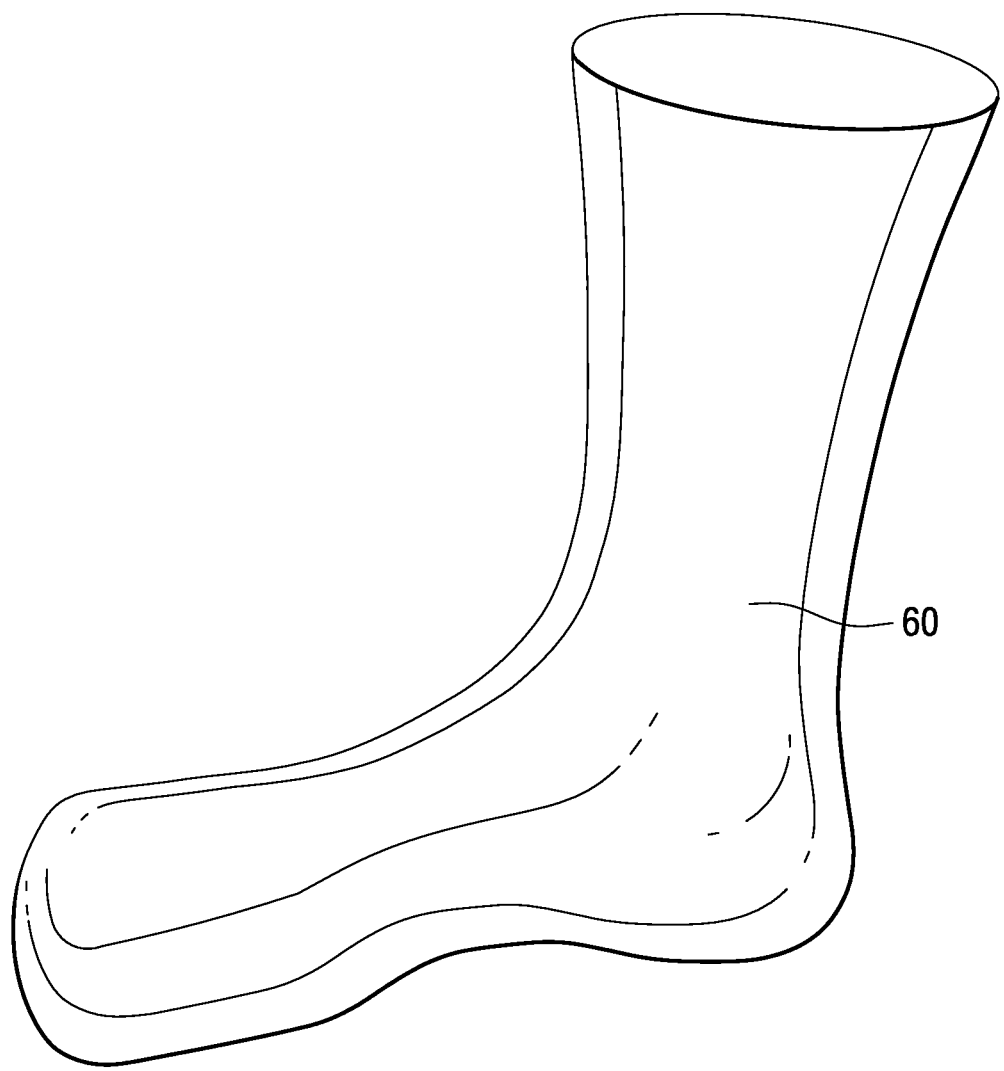
FIG. 9 shows an illustration of a replica mold of a foot and ankle as used in the preferred method.
Figure 11:
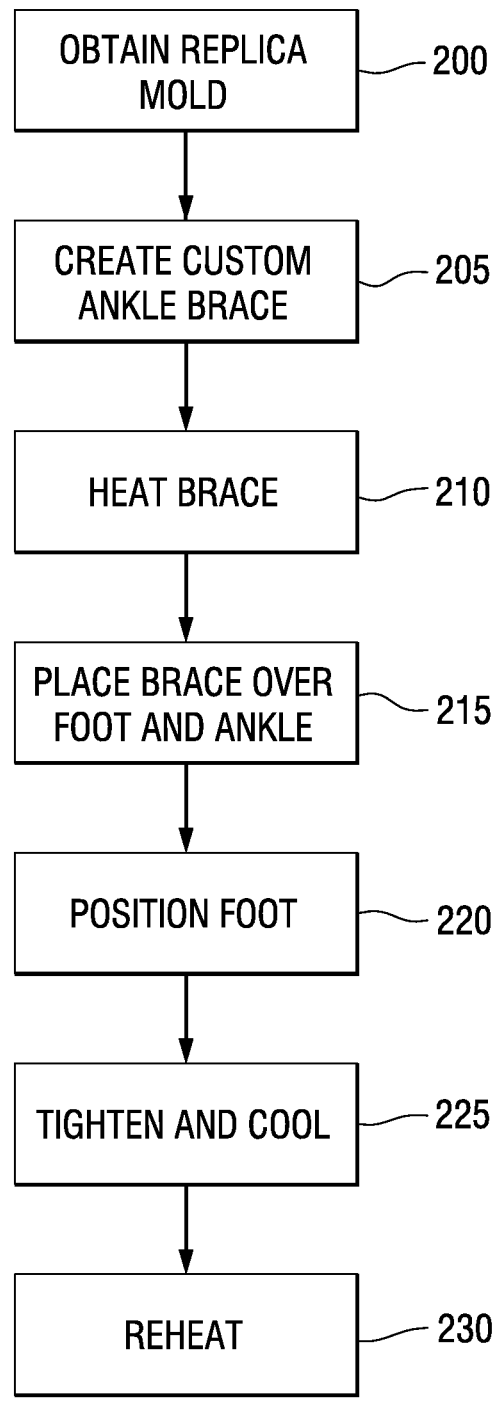
FIG. 11 shows an illustration of a diagram of an example of additional steps in the preferred method.

FIGS. 8-10 illustrate a preferred method of making the custom ankle brace system 2 of the invention. FIG. 8 shows an illustration of a diagram of an example of the steps in the preferred method. The first step 100 in making ankle brace 2 is preparing a replica mold 60 of the foot and ankle. Such a replica mold is illustrated in FIG. 9. Replica mold 60 is produced from the foot and ankle of the patient for which ankle brace 2 will be prepared. This allows for the production of a fully custom ankle brace 2. The replica mold 60 is formed from a cast produced by a professional skilled in producing replica models for the production of orthotics. In another embodiment, replica mold 60 may be created based on a series of measurements provided by a professional. These measurements are entered into specialty computer programs, for instance Computer Aided Design (CAD) programs, which will produce a duplicate of the foot and ankle. Replica mold 60 is then produced with the assistance of the CAD program.

Next in step 105 inner liner 10 is cut to an appropriate size to cover the replica mold 60. Inner liner 10 is cut to cover the foot, ankle, lower calf, upper foot and mid foot and an opening for the toes 4. One of ordinary skill in the art will understand that alternative configurations of inner liner 10 are contemplated, for instance an inner liner that does not cover the entire upper foot, or calf area, or a liner that completely or partially covers the toe area.

Next, the posterior section of inner liner 10 is folded and sewn together to provide a seam 6 as shown in step 110. Seam 6 is open down the entire front or anterior of ankle brace 2. Multiple seams 6 may be utilized, for instance in the case of a larger foot. After any excess material is removed, inner liner 10 is moistened with a 50/50 mixture of 70% isopropyl alcohol and water and stretched over replica mold 60 (step 110). This fluid allows for the material to stretch properly over the mold in order to eliminate wrinkles or folding. Other fluid mixtures may be available to aid in the placement of inner liner 10. Inner liner 10 is positioned to cover the entire foot, heel, ankle and lower calf, but may be constructed in alternative configurations, as discussed previously. Next, as illustrated in step 120, inner liner 10 is stapled or nailed directly down the center of the anterior of the mold. Excess material is then cut and removed from inner liner 10.

As illustrated in step 125, the medial malleolus, lateral malleolus and navicular foam pads 12 are cut and secured to inner liner 10 with an adhesive as illustrated in FIGS. 3A, 3B and 3C. One of skill in the art will understand that additional pads may be placed on other portions of the ankle, foot or calf as needed to prevent rubbing or chaffing. In step 130 nylon stockings are stretched over inner lining 10 and foam pads 12. The stockings are taped to a vacuum mandrel and then covered with a vacuum bag or equivalent. The application of a vacuum applies pressure to inner lining 10 and foam pads 12 while the adhesive tacks.

Next, as illustrated in step 135, a flat piece of non-olefinic elastomeric blend polymer material is cut and placed in an oven. One of skill in the art will recognize that other methods of heating the plastic would be acceptable, for instance with a heat gun or equivalent. The non-olefinic thermoplastic may be softened and molded with dry heat, thus making the use of boiling liquids unnecessary. The non-olefinic thermoplastic material becomes soft and manageable when heated as described, but continues to maintain its integrity and does not permanently self stick. At step 140, the softened non-olefinic thermoplastic material is draped over inner liner 10 and foam pads 12. With the use of nylon stockings, the non-olefinic thermoplastic is vacuumed sealed around the inner liner 10 and foam pads 12. After cooling, the non-olefinic thermoplastic is removed from the inner liner 10 and foam pads 12, resulting in the rough equivalent of the thermoplastic support 20 as described above. Next, at step 145, the final thermoplastic support 20 is created by tracing and cutting a proximal trim line approximately 6 inches from the apex of the medial malleolus, with the anterior edge totally encompassing the medial malleolus 70, navicular 74, and lateral malleolus 72, as illustrated in FIGS. 10A and 10B. As illustrated in FIGS. 10C and 10D, heel cut-out 30 is traced and cut so that the plantar portion of the calcaneus is encompassed by thermoplastic support 20 while the posterior edge 76 is open for approximately 4 inches up the calf. Heel cut-out 30 may then be covered by a foam pad 12 to prevent rubbing or chafing. One of skill in the art will recognize that the invention is not limited to the dimensions as described above and alternative embodiments, such as the absence of heel cut-out 30 or differences in the size and placement of foam pads 20, are contemplated.

At step 150, the now-finished thermoplastic support 20 is attached to inner liner 10 and foam pads 12 by the use of a polyurethane adhesive or equivalent, as described previously. The ankle brace 20, now comprising inner liner 10, foam pads 12 and thermoplastic support 20 is then vacuum sealed with a vacuum bag for approximately 15-30 minutes to allow the adhesive to properly tack. At step 155, flexible outer layer 40 is moistened with a 50/50 mixture of 70% isopropyl alcohol and water as described above. Flexible outer layer 40 is stretched over and adhered to ankle brace 2 using a polyurethane adhesive or equivalent as described previously. The device is then vacuum sealed with a vacuum bag for approximately 15-30 minutes to allow the adhesive to properly tack.

As illustrated in step 160, ankle brace 2 is removed from replica mold 60 by cutting along seam 6. The edges of flexible outer layer may then be finished, for instance, by sewing or other methods. Next, closure apparatus 8 is added to edge of seams 6. In one embodiment, closure apparatus 8 includes eyelets 44 for receiving laces 46. Closure apparatus 8 may also comprise straps, snaps, Velcro or other materials, which will also be added along the edge of seam 6.

Tongue 48 is then constructed as illustrated in step 165. Tongue 48 may be constructed of a variety of materials know in the art, such materials being soft but strong and flexible. In one embodiment, tongue 48 is constructed from headliner foam and flexible microfiber synthetic high abrasion resistance fabric attached through the use of adhesive and/or stitches as described above. Tongue 48 is attached, for example, to the lower anterior side of ankle brace 2 by sewing in the corner at approximately 1½ inch. In an additional embodiment, tongue 48 may be attached to one side or both sides of the brace.

FIG. 10 is an illustration of a diagram of an example of the preferred step of a method of using the custom ankle brace 2 according to the present invention. A first step 200 is to obtain a replica mold 60 of the foot and ankle of the patient for whom the ankle brace is constructed. The replica mold 60 may be created using a number of methods as described above. At step 205 a custom ankle brace 20 is constructed from the replica mold 60, as described in detail previously. Next, at step 210, the completed custom ankle brace 2 is heated to a temperature of about 150° F. to 200° F. for approximately 8 to 12 min. Ankle brace 2 may be heated by a number of methods, for instance with an oven or a heat gun. The custom ankle brace 2 of the invention may be heated utilizing a non-liquid medium, thus preserving the integrity of the lining materials in ankle brace 2. The heating step allows the custom ankle brace 2 to become soft and flexible while still retaining its general shape so that it can be fitted to the individual patient.

The ankle brace 2 may now be custom fitted to the patient for whom it was constructed. This fitting is generally done by a professional with experience with orthotics, for instance an orthotist, prosthetist, podiatrist, orthopedist or a physical therapist. At step 215 the heated custom ankle brace 2 is placed over the foot and ankle of the individual for whom it was constructed. A sock may be worn by the individual during the molding and fitting process. At step 220, the patient's foot and ankle are placed in the clinically desirable position for which the brace has been developed. This may be accomplished, for example, by resting the foot on the floor from a sitting position or placing the foot in the proper position while standing. The experienced professional then tightens closure apparatus 8 so that it fits securely on the foot, as illustrated at step 225. If necessary, ankle brace 2 may be further fitted to the foot by wrapping and compressing with a bandage or wrap. Ankle brace 2 is then allowed to cool for approximately 15 to 30 minutes until it cools to room temperature. The thermoplastic support 20 then becomes rigid and retains the clinically desired shape as prescribed by the experienced professional. Because of the properties of thermoplastic support as described above, ankle brace 2 may be readjusted, remolded and refitted as needed, as illustrated in step 230, to account for growth, swelling or other changes to the affected foot and/or ankle, or to provide for additional comfort. This procedure results in a custom ankle brace that was specifically constructed and adjusted for a given patient.

While the invention has been described in connection with certain embodiments, it is not intended to limit the scope of the invention to the particular forms set forth, but, on the contrary, it is intended to cover such alternatives, modifications, and equivalents as may be included within the spirit and scope of the invention as defined by the appended claims.

The invention claimed is:

1. An ankle brace comprising:
   a. a non-olefinic elastomeric blend thermoplastic polymer support having:
      i. a back portion extending substantially circumferentially around a posterior section of a user's lower leg; and
      ii. a sole portion extending outwardly from and integrally formed with said back portion, said sole portion formed to be mounted adjacent to and supporting substantially all of a sole and heel of the user's foot;
   b. an inner liner;
   c. a foam pad attached to an exterior surface of the inner liner, wherein the foam pad covers a portion of the exterior surface of the inner liner but does not cover the entire exterior surface of the inner liner, wherein the exterior surface is the surface of the inner liner that is farthest from the portion of the user around which the inner liner is disposed;
   d. a flexible outer layer that engages the exterior surface of the inner liner and that engages the foam pad and the support; and
   e. a heel cut-out portion.

2. The ankle brace of claim 1 wherein said inner liner and said flexible outer layer further comprise a closure apparatus.

3. The ankle brace of claim 2 wherein said closure apparatus comprises eyelets and laces.

4. The ankle brace of claim 1 further comprising a tongue.

5. The ankle brace of claim 1 further comprising a toeless portion.

6. An ankle brace comprising:
   a. a non-olefinic elastomeric blend thermoplastic polymer support having:

i. a back portion extending substantially circumferentially around a posterior section of a user's lower leg; and
    ii. a sole portion extending outwardly from and integrally formed with said back portion, said sole portion formed to be mounted adjacent to and supporting substantially all of a sole and heel of the user's foot;
  b. an inner liner;
  c. a foam pad attached to an exterior surface of the inner liner, wherein the foam pad covers a portion of the exterior surface of the inner liner but does not cover the entire exterior surface of the inner liner, wherein the exterior surface is the surface of the inner liner that is farthest from the portion of the user around which the inner liner is disposed;
  d. a flexible outer layer that engages the exterior surface of the inner liner and that engages the foam pad and the support;
  wherein the support, inner liner, foam pad, and outer layer are heated and placed onto the user's foot and molded, and wherein the support, inner liner, foam pad, and outer layer are subsequently reheated and replaced onto the user's foot and remolded; and
  e. a moveable ankle joint.

7. A method of making an ankle brace system comprising:
  a. covering a replica mold of the relevant appendage provided with an inner lining;
  b. attaching foam pads to an exterior surface of the inner lining such that the foam pads cover a portion of the exterior surface of the inner lining but do not cover the entire exterior surface of the inner lining, wherein the exterior surface is the surface of the inner lining that is farthest from the portion of the replica mold around which the inner lining is disposed when the inner lining is disposed around the replica mold;
  c. heating a non-olefinic elastomeric blend polymer material support device to a moldable temperature, creating a support and;
  d. molding and securing said non-olefinic elastomeric blend polymer support to said inner lining and said foam pads to create a thermoplastic support device, said thermoplastic support device comprising
    i. a back portion extending substantially circumferentially around the posterior section of a user's lower leg; and
    ii. a sole portion extending outwardly from and integrally formed with said back portion, said sole portion formed to be mounted adjacent to and supporting substantially all of a sole and heel of the user's foot
  e. placing a flexible outer layer over the thermoplastic support device such that the outer layer engages the exterior surface of the inner lining and one of the foam pads and the support;
  f. heating the support, inner lining, foam pads, and outer layer and placing the support, inner lining, foam pads, and outer layer onto the user's foot and molding the support when on the user's foot; and
  g. subsequently reheating the support, inner lining, foam pads and outer layer and replacing the support, inner lining, foam pads, and outer layer onto the user's foot and remolding the support when on the user's foot.

8. The method of claim 7, wherein said foam pads are attached to said inner lining by an adhesive such that the adhesive is located between the foam pads and the inner lining.

9. The method of claim 7 further comprising securing a closure apparatus to said inner lining and said flexible outer layer.

10. The method of claim 9 wherein said closure apparatus comprises eyelets and laces.

11. The method claim 7 further comprising securing a tongue to said ankle brace.

12. The method of claim 7 further comprising creating a heel cut-out portion in said thermoplastic support.

13. The method of claim 7 further comprising creating a toeless portion in said thermoplastic support.

14. The method of claim 7 further comprising creating a moveable ankle joint in said thermoplastic support.

15. The method of claim 7 further comprising securing a securing mechanism in said thermoplastic support.

16. The method of claim 7, further comprising selecting a non-olefinic elastomeric blend thermoplastic polymer material which is moldable at a temperature appropriate for affixing said ankle brace system to the user while molding.

17. A method of fitting an ankle brace system, comprising
  a. preparing an ankle brace comprising a non-olefinic elastomeric blend polymer material support constructed of a material of sufficient rigidity to support said ankle comprising:
    i. a back portion extending substantially circumferentially around the posterior section of a user's lower leg; and
    ii. a sole portion extending outwardly from and integrally formed with said back portion, said sole portion formed to be mounted adjacent to and supporting substantially all of a sole and heel of the user's foot;
  b. providing an inner lining;
  c. attaching foam pads to an exterior surface of the inner lining such that the foam pads cover a portion of the exterior surface of the inner lining but do not cover the entire exterior surface of the inner lining, wherein the exterior surface is the surface of the inner lining that is farthest from the portion of the user around which the inner lining is disposed when the inner lining is disposed around the portion of the user;
  d. placing a flexible outer layer over the thermoplastic support device such that the outer layer engages the exterior surface of the inner lining and one of the foam pads and the support;
  e. heating said ankle brace to a temperature appropriate for molding;
  f. placing the foot and ankle of the user in a clinically desirable position;
  g. compressing and fitting said heated ankle brace on the limb of the user until said ankle brace has cooled to room temperature, wherein said heated ankle brace engages said foam pads; and
  h. removing said ankle brace and subsequently reheating the support, inner lining, foam pads and outer layer and replacing the support, inner lining, foam pads, and outer layer onto the user's foot and remolding the support when on the user's foot.

18. A method of making an ankle brace system comprising:
  a. covering a mold of the relevant appendage provided with an inner lining;
  b. attaching foam pads to an exterior surface of the inner lining such that the foam pads cover a portion of the exterior surface of the inner lining but do not cover the entire exterior surface of the inner lining, wherein the exterior surface is the surface of the inner lining that is farthest from the portion of the mold around which the inner lining is disposed when the inner lining is disposed around the mold;
c. heating a non-olefinic elastomeric blend polymer material support device to a moldable temperature, creating a support and;
d. molding and securing said non-olefinic elastomeric blend polymer support to said inner lining and said foam pads to create a thermoplastic support device, said thermoplastic support device comprising
   i. a back portion extending substantially circumferentially around the posterior section of a user's lower leg; and
   ii. a sole portion extending outwardly from and integrally formed with said back portion, said sole portion formed to be mounted adjacent to and supporting substantially all of a sole and heel of the user's foot;
e. heating the support, inner lining, and foam pads and placing the support, inner lining, and foam pads onto the user's foot and molding the support when on the user's foot; and
f. subsequently reheating the support, inner lining, and foam pads and replacing the support, inner lining, and foam pads onto the user's foot and remolding the support when on the user's foot.

* * * * *